United States Patent [19]

Bradfisch et al.

[11] Patent Number: 5,208,017
[45] Date of Patent: May 4, 1993

[54] **BIOLOGICALLY ACTIVE *BACILLUS THURINGIENSIS* ISOLATES**

[75] Inventors: Gregory A. Bradfisch, San Diego; Tracy Michaels, Escondido; Jewel M. Payne, San Diego, all of Calif.

[73] Assignee: Mycogen Corporation, San Diego, Calif.

[21] Appl. No.: 710,890

[22] Filed: Jun. 6, 1991

Related U.S. Application Data

[63] Continuation-in-part of Ser. No. 658,934, Feb. 21, 1991, abandoned.

[51] Int. Cl.$^5$ .................. A01N 25/00; C12N 3/00
[52] U.S. Cl. .................. 424/84; 424/93 L; 435/242; 514/2
[58] Field of Search .................. 424/93, 84; 435/242; 514/2

[56] References Cited

U.S. PATENT DOCUMENTS

| | | | |
|---|---|---|---|
| 4,764,372 | 8/1988 | Herrnstadt et al. | 424/93 |
| 4,771,131 | 9/1988 | Herrnstadt et al. | 435/254 |
| 4,797,276 | 1/1989 | Herrnstadt et al. | 424/93 |
| 4,849,217 | 7/1989 | Soares et al. | 424/93 |

OTHER PUBLICATIONS

Couch, T. L., (1980) "Mosquito Pathogenicity of B.t. var. *israelensis*" *Developments in Industrial Microbiology* 22:61–76.

Beegle, C. C. (1978) "Use of Entomogenous Bacteria in Agroecosystems" *Developments in Industrial Microbiology* 20:97–104.

*Primary Examiner*—Douglas W. Robinson
*Assistant Examiner*—Deborah K. Ware
*Attorney, Agent, or Firm*—Saliwanchik & Saliwanchik

[57] ABSTRACT

Disclosed and claimed are *Bacillus thuringiensis* isolates designated *B.t.* PS86A1 and *B.t.* PS86Q3, which are active against corn rootworm larvae and the alfalfa weevil. Thus, these isolates, or mutants thereof, can be used to control such pests. Further, genes encoding novel δ-endotoxins can be removed from these isolates and transferred to other host microbes, or plants. Expression of the δ-endotoxins in such hosts results in the control of corn rootworm larvae and the alfalfa weevil.

17 Claims, 3 Drawing Sheets

Figure 1

| 155 kDa |
| 135 kDa |
| 98 kDa |
| 62 kDa |
| 58 kDa | 58 kDa |
| | 45 kDa |

A    B

A. *Bacillus thuringiensis* PS86Q3

B. *Bacillus thuringiensis* PS86A1

Figure 2-1

|   |   |
|---|---|
|   | 205 kDa |
|   | 116 kDa |
|   | 97.4 kDa |
|   | 66 kDa |
|   | 45 kDa |
|   | 29 kDa |

A   B   C   D   E   F   G   H

A. *Bacillus thuringiensis* PS17
B. *Bacillus thuringiensis* PS33F2
C. *Bacillus thuringiensis* PS45B1
D. *Bacillus thuringiensis* PS52A1
E. *Bacillus thuringiensis* PS62B1
F. *Bacillus thuringiensis* PS74G1
G. *Bacillus thuringiensis* PS86Q3
H. Molecular Weight Standard

Figure 2-2

205 kDa
116 kDa
97.4 kDa
66 kDa
45 kDa
29 kDa

I  J  K  L  M  N  O  P

I. *Bacillus thuringiensis* PS84C3
J. *Bacillus thuringiensis* PS86A1
K. *Bacillus thuringiensis* PS98A3
L. *Bacillus thuringiensis* PS80JJ1
M. *Bacillus thuringiensis* PS80PP3
N. *Bacillus thuringiensis* PS80PP4
O. *Bacillus thuringiensis* PS86Q3
P. Molecular Weight Standard

BIOLOGICALLY ACTIVE *BACILLUS THURINGIENSIS* ISOLATES

CROSS-REFERENCE TO A RELATED APPLICATION

This is a continuation-in-part of co-pending application Ser. No. 07/658,934 filed on Feb. 21, 1991, now abandoned.

BACKGROUND OF THE INVENTION

Many hundreds of strains of *Bacillus thuringiensis* (*B.t.*) produce insecticidal toxins designated as delta endotoxins. They are synthesized by sporulating *B.t.* cells. When toxin is ingested by a susceptible insect, the cells of the gut epithelium are destroyed.

The reported activity spectrum of *B.t.* covers insect species within the orders Lepidoptera and Coleoptera, many of which are major pests in agriculture and forestry. The activity spectrum also includes the insect order Diptera, which includes mosquitoes and black flies. See Couch, T. L. (1980) "Mosquito Pathogenicity of *Bacillus thuringiensis* var. *israelensis*," Developments in Industrial Microbiology 22:61–76; Beegle, C. C. (1978) "Use of Entomogenous Bacteria in Agroecosystems," Developments in Industrial Microbiology 20:97–104. Dipteran insects are serious nuisances as well as being vectors of many serious human and animal diseases such as malaria, onchocerciasis, equine encephalitis, and dog heartworm.

Approximately 9.3 million acres of U.S. corn is infested with the corn rootworm species complex, which includes the northern corn rootworm, *Diabrotica barberi*, the southern corn rootworm, *D. undecimpunctata howardi*, and the western corn rootworm, *D. virgifera virgifera*. The soil-dwelling larvae of these Diabrotica species feed on corn root, causing lodging of the corn plant. This eventually results in yield reduction or death of the plant. By feeding on cornsilks, the adults reduce pollination and, therefore, the yield of corn per plant. In addition, adults and larvae of the southern corn rootworm, also known as the spotted cucumber beetle, attack cucurbit crops (cucumbers, melons, squash, etc.) and many vegetable and field crops in commercial production as well as in home gardens.

Control of the corn rootworm has been partially addressed by cultural methods, such as crop rotation and application of high nitrogen levels to stimulate the growth of adventitious root systems. However, chemical insecticides are relied upon heavily to guarantee the desired level of control. Insecticides are banded onto the soil or incorporated into the soil. The major problem associated with the use of these chemicals is the development of resistance among the treated insect populations.

U.S. Pat. No. 4,849,217 discloses *Bacillus thuringiensis* isolates active against the alfalfa weevil.

The alfalfa weevil, *Hypera postica*, and the closely related Egyptian alfalfa weevil, *Hypera brunneipennis*, are the most important insect pests of alfalfa grown in the United States, with 2.9 million acres infested in 1984. An annual sum of 20 million dollars is spent to control these pests. The Egyptian alfalfa weevil is the predominant species in the southwestern U.S., where it undergoes aestivation (i.e., hibernation) during the hot summer months. In all other respects, it is identical to the alfalfa weevil, which predominates throughout the rest of the U.S.

The larval stage is the most damaging in the weevil life cycle. By feeding at the alfalfa plant's growing tips, the larvae cause skeletonization of leaves, stunting, reduced plant growth, and, ultimately, reductions in yield. Severe infestations can ruin an entire cutting of hay. The adults, also foliar feeders, cause additional, but less significant, damage.

Chemical insecticides play a major role in effective alfalfa weevil control. However, there are several problems associated with their use including:

1. acute mammalian toxicity: several of the most effective insecticides used for weevil control are highly toxic to humans and other mammals, and are sold on a restricted basis in many states. Toxic residues are an additional problem for hay sold as feed for livestock.

2. honeybee toxicity: the honeybee is sensitive to some of the insecticides used for alfalfa weevil control. Because alfalfa is the major source of nectar for commercial honeybee colonies in the U.S., the use of insecticides with honeybee toxicity is incompatible with the needs of the honey producers.

3. toxicity to natural enemies: the insect parasites and predators which normally help control populations of minor alfalfa pests (aphids, spider mites, leafhoppers, caterpillars) are highly susceptible to all insecticides presently used for alfalfa weevil control. Reductions in the numbers of beneficial insects can result in increased populations of these once minor pests (secondary pests outbreaks), and in the consequent application of additional insecticides. Secondary pest outbreaks of aphids and mites often lead to serious yield reductions.

At present there is a need for more effective control agents, particularly efficacious agents that act selectively and do not cause the secondary outbreaks of mites and aphids that can be so devasting to alfalfa.

BRIEF SUMMARY OF THE INVENTION

The subject invention concerns novel *Bacillus thuringiensis* isolates which have activity against corn rootworm larvae (*Diabrotica undecimpunctata undecimpunctata*) and the Egyptian Alfalfa weevil (*Hypera brunneipennis*).

Specifically, the invention comprises *B.t.* isolates designated *B.t.* PS86A1 and *B.t.* PS86Q3, and mutants thereof, and novel delta endotoxin genes obtainable from these *B.t.* isolates which encode proteins which are active against corn rootworm larvae and the Egyptian alfalfa weevil. The *B.t.* microbes and the transformed microbes, disclosed herein, can be used alone or in mixtures thereof.

BRIEF DESCRIPTION OF THE DRAWINGS

FIG. 1 is a photograph of a 9% SDS polyacrylamide gel showing alkalisoluble proteins of *B.t.* PS86Q3 and *B.t.* PS86A1.

FIG. 2 is a photograph of a standard SDS polyacrylamide gel showing alkali-soluble proteins of alfalfa weevil-active *B.t.* strains. All the *B. thuringiensis* strains are disclosed in U.S. Pat. No. 4,849,217, except *B. thuringiensis* PS86Q3 which is disclosed herein.

DETAILED DISCLOSURE OF THE INVENTION

The *Bacillus thuringiensis* isolates of the subject invention have the following characteristics:

*B.t.* PS86A1

Colony morphology—large colony, dull surface, typical B.t.
Vegetative cell morphology—typical B.t.
Culture methods—typical for B.t.
Activity—inclusions kill corn rootworm larvae and alfalfa weevil larvae
Inclusion type—multiple attached
Molecular weight of proteins (kDa)—58, 45

B.t. PS86Q3
Colony morphology—large colony, dull surface, typical B.t.
Vegetative cell morphology—typical B.t.
Culture methods—typical for B.t.
Activity—inclusions kill corn rootworm larvae and alfalfa weevil larvae
Inclusion type—long attached
Molecular weight of proteins (kDa)—155, 135, 98, 62, 58

The B.t. isolates of the invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and mutants thereof, can be used to control pests as disclosed herein.

The cultures of the subject invention were deposited in the Agricultural Research Service Patent Culture Collection (NRRL), Northern Regional Research Center, 1815 North University Street, Peoria, Ill. 61604 USA.

| Culture | Accession No. | Deposit date |
|---|---|---|
| Bacillus thuringiensis PS86A1 | NRRL B-18400 | August 16, 1988 |
| Bacillus thuringiensis PS86Q3 | NRRL B-18765 | February 6, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

The subject cultures were deposited in an acknowledged highly qualified culture repository. The invention also includes deposits of the same cultures in other culture repositories. Thus, the disclosure and claims are not limited to the specific culture accession number(s) disclosed herein. Also, within this invention are deposits at other repositories which can be shown to have the same biological activity characteristics of the culture(s) disclosed herein.

The toxin genes harbored by the novel isolates of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of corn rootworm larvae or the alfalfa weevil where they will proliferate and be ingested by the larvae or weevil. The result is a control of these pests. Alternatively, the microbe hosting the toxin gene can be treated under conditions that prolong the activity of the toxin produced in the cell. The treated cell then can be applied to the environment of the target pest. The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the soil. These microorganisms are selected so as to be capable of successfully competing in the soil with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae. Of particular interest are such phytosphere bacterial species as Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii; and phytosphere yeast species such as Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae, and Aureobasidium pollulans. Of particular interest are the pigmented microorganisms.

A wide variety of ways are available for introducing a *B.t.* gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 5000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi, as disclosed previously.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells of the invention can be cultured using standard art media and fermentation techniques. Upon completion of the fermentation cycle the bacteria can be harvested by first separating the *B.t.* spores and crystals from the fermentation broth by means well known in the art. The recovered *B.t.* spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulated bait granules containing an attractant and spores and crystals of the *B.t.* isolates, or recombinant microbes comprising the gene(s) obtainable from the *B.t.* isolates disclosed herein, can be applied to the soil. Formulated product can also be applied as a seed-coating or root treatment or total plant treatment at later stages of the crop cycle.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the alfalfa weevil or the corn rootworm larvae, e.g., soil, by spraying, dusting, sprinkling, or the like.

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at the time, numerous colonies could be growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of the *B.t.* Isolates

A subculture of the *B.t.* isolates, or mutants thereof, can be used to inoculate the following medium, a peptone, glucose, salts medium.

| | | |
|---|---|---|
| Bacto Peptone | 7.5 | g/l |
| Glucose | 1.0 | g/l |
| $KH_2PO_4$ | 3.4 | g/l |
| $K_2HPO_4$ | 4.35 | g/l |
| Salt Solution | 5.0 | ml/l |
| $CaCl_2$ Solution | 5.0 | ml/l |
| pH 7.2 | | |
| Salts Solution (100 ml) | | |
| $MgSO_4.7H_2O$ | 2.46 | g |
| $MnSO_4.H_2O$ | 0.04 | g |
| $ZnSO_4.7H_2O$ | 0.28 | g |
| $FeSO_4.7H_2O$ | 0.40 | g |
| $CaCl_2$ Solution (100 ml) | | |
| $CaCl_2.2H_2O$ | 3.66 | g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Activity of *B.t.* Isolates Against Corn Rootworm Larvae

*B.t.* isolates PS86Q3 and PS86A1 can be grown using known media and culturing techniques. Spore/crystal preparations are obtained by centrifuging broths and reconstituting pellets with a 0.05% aqueous solution of SILWET ® (Union Carbide Corp.) surfactant (L-77) at a 20-fold concentration of the original broth. Fifty µl of this solution is then pipetted onto 1 ml of artificial diet in wells of a standard 24 well assay plate. One first instar *D. undecimpunctata undecimpunctata* larva was added to each well.

Growth was measured by weighing larvae at the end of a 5-8 day assay period. Growth reduction (G.R.) was determined according to the formula:

$$G.R. = (1 - T/C)*100$$

where,
C = mass of control larvae (mg) and,
T = mass of treated larvae (mg).

Both *B.t.* PS86A1 and PS86Q3 decreased the rate of growth of *D.u. undecimpunctata* (Table 1).

TABLE 1

Decreased rate of growth of *Diabrotica undecimpunctata undecimpunctata* fed diet treated with *Bacillus thuringiensis* isolates

| Isolate | Inclusion | Major Proteins (kDa) | Growth Reduction (%) |
|---|---|---|---|
| PS86A1 | Attached multiple | 58, 45 | 86 |
| PS86Q3 | Attached long | 155, 135, 98, 62, 58 | 83 |

EXAMPLE 3

Activity of *B.t.* PS86Q3 Against the Egyptian alfalfa weevil

The *B. thuringiensis* isolate PS86Q3 was tested as a spray-dried powder of a fermentation broth which was concentrated by centrifugation. Pellets, which consist of water and biomass (spores, crystalline δ-endotoxins, cellular debris and growth media) were mixed with a standard carrier, preservative and surfactant. The powders, which consisted of 25% biomass, were made using a Yamato spray drier. (Sold by Yamato Scientific Co., Ltd. Tokoyo, Japan).

Approximately two ml of a 1.5% agar diet is added to each well of a Corning Cell Wells ™ 24 well assay plate (Corning Glass Works, Corning, New York). The trays containing diet are dried under an air hood. Spray dried powder of PS86Q3 is suspended in water at 100 mg substance/ml. 50 µl of the suspension is pipetted onto the diet. The trays are then placed in a clean air hood until completely dry. One second instar larvae of Alfalfa weevil, *Hypera brunneipennis* was placed in each well. The infested trays are covered with a sheet of polyolentreated Mylar and heat sealed with a tacking iron. The Mylar covering is pierced carefully with minute pins (four holes per well) and the tray is held in an incubator at 25° C. Evaluation for mortality is determined at six days.

| Toxicity of *B.t.* sprayed-dried powder PS86Q3 to second instar alfalfa weevil, *Hyper brunneipennis* | |
|---|---|
| *B.t.* | Percent Mortality |
| PS86Q3 | 79% |
| Control | 8% |

*The artificial diet is as follows:

EXAMPLE 4

Insertion of Toxin Genes Into Plants

The novel genes, obtainable from the *B.t.* isolates of the invention, coding for the novel toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5

Cloning of Novel *B. thuringiensis* Genes Into Baculoviruses

The novel genes, obtainable from the *B.t.* isolates of the invention, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin can be modified with BamHI linkers at appropriate regions both upstream and downstream from the coding region and inserted into the passenger site of one of the AcNPV vectors.

We claim:

1. A process for controlling corn rootworm larvae which comprises incorporating in the soil habitat of said corn rootworm larvae a corn rootworm larvae-controlling amount of *Bacillus thuringiensis* PS86A1 NRRL B-18900 or PS86Q3 NRRL B-1876, and mutants thereof which retain the activity against the corn rootworm, or spores of said microbes.

2. A process, according to claim 1, which comprises incorporating said *Bacillus thuringiensis* microbes, or spores from said microbes, into a bait granule and placing said granule on or in the soil when planting seeds of corn, or at later stages of the crop cycle.

3. The process, according to claim 1, wherein said microbe is *Bacillus thuringiensis* PS86A1 NRRL B-18400.

4. The process, according to claim 1, wherein said microbe is *Bacillus thuringiensis* PS86Q3 NRRL B-18765.

5. A method for controlling corn rootworm larvae which comprises contacting said larvae with a corn rootworm larvae-controlling amount of a *Bacillus thuringiensis* selected from the group consisting of *Bacillus thuringiensis* PS86A1, NRRL B-18400 and *Bacillus thuringiensis* PS86Q3, NRRL B-18765.

6. A composition of matter comprising a *Bacillus thuringiensis* mutant prepared from parent *Bacillus thuringiensis* PS86A1, NRRL B-18400 or *Bacillus thuringiensis* PS86Q3, NRRL B-18765, in association with an inert carrier.

7. A composition of matter for controlling corn rootworm comprising *Bacillus thuringiensis* PS86A1, NRRL B-18400 and *Bacillus thuringiensis* PS86Q3, NRRL B-18765, and mutants thereof which retain the activity against the corn rootworm, or spores of said microbes, in association with an inert carrier.

8. A composition of matter, according to claim 7, comprising *Bacillus thuringiensis* PS86Q3 NRRL B-18765.

9. A pesticidal composition comprising substantially intact, treated cells having prolonged pesticidal activity and greater persistence in the feeding zone when applied to the environment of a target pest, wherein said pesticide is produced by *Bacillus thuringiensis* PS86A1, NRRL B-18400 or *Bacillus thuringiensis* PS86Q3, NRRL B-18765.

10. The pesticidal composition, according to claim 9, wherein said microbe is *Bacillus thuringiensis* PS86A1 NRRL B-18400.

11. The pesticidal composition, according to claim 9, wherein said microbe is *Bacillus thuringiensis* PS86Q3 NRRL B-18765.

12. A method for controlling corn rootworm larvae which comprises contacting said larvae with a corn rootworm larvae-controlling amount of a pesticidal composition comprising intact treated cells having prolonged pesticidal activity when applied to the environment of corn rootworm larvae, wherein said insecticide is produced by *Bacillus thuringiensis* PS86A1, NRRL B-18400 or *Bacillus thuringiensis* PS86Q3, NRRL B-18765.

13. The method, according to claim 12, wherein said microbe is *Bacillus thuringiensis* PS86A1 NRRL B-18400.

14. The method, according to claim 12, wherein said microbe is *Bacillus thuringiensis* PS86Q3 NRRL B-18765.

15. A biologically pure culture of *Bacillus thuringiensis* PS86Q3 having all the identifying characteristics of deposit NRRL B-18765.

16. A process for controlling insect infestation of alfalfa, said infestation by an alfalfa weevil, which comprises contacting said infesting insect, or treating the environment of said infesting insect, with an alfalfa weevil-controlling amount of *Bacillus thuringiensis* PS86Q3, NRRL B-18765, or mutants thereof which retain the activity against the alfalfa weevil, or spores from said *Bacillus thuringiensis* microbe.

17. The process, according to claim 16, wherein said alfalfa weevil is the Egyptian alfalfa weevil (EAW).

* * * * *

UNITED STATES PATENT AND TRADEMARK OFFICE
CERTIFICATE OF CORRECTION

PATENT NO. : 5,208,017
DATED : May 4, 1993
INVENTOR(S) : Gregory A. Bradfisch, Tracy Michaels, and Jewel Payne It is certified that error appears in the above-indentified patent and that said Letters Patent is hereby corrected as shown below:

Column 2, line 57, "alkalisoluble" should read --alakalisoluble" should read --alakali-soluble--.

Column 11, line 40, "B-18900 or PS86Q3 NRRL B-1876" should read --B-18400, or PS86Q3, NRRL B-18765--.

Signed and Sealed this

Eighth Day of February, 1994

Attest:

BRUCE LEHMAN

Attesting Officer

Commissioner of Patents and Trademarks